United States Patent [19]

Tosic

[11] Patent Number: 5,928,230
[45] Date of Patent: Jul. 27, 1999

[54] ARTICULATED EXTERNAL ORTHOPEDIC FIXATION SYSTEM AND METHOD OF USE

[76] Inventor: Aleksandar Tosic, 7304 Hampshire Dr., Apartment 4, St. Louis, Mo. 63109

[21] Appl. No.: 09/014,051

[22] Filed: Jan. 27, 1998

Related U.S. Application Data

[62] Division of application No. 08/717,224, Sep. 26, 1996.
[51] Int. Cl.[6] .................................................. A61B 17/66
[52] U.S. Cl. .............................................. 606/57; 606/56
[58] Field of Search ................................. 606/54, 55, 56, 606/57, 58, 59, 60, 61, 63, 72, 73

[56] References Cited

U.S. PATENT DOCUMENTS

| | | | |
|---|---|---|---|
| 4,308,863 | 1/1982 | Fischer | 606/57 |
| 4,450,834 | 5/1984 | Fischer | 606/80 |
| 4,889,111 | 12/1989 | Ben-Dov | 606/56 |
| 4,890,631 | 1/1990 | Hardy | 606/59 |
| 4,923,458 | 5/1990 | Fischer | 606/59 |
| 5,352,224 | 10/1994 | Westermann | 606/61 |
| 5,514,143 | 5/1996 | Bonutti et al. | 606/86 |
| 5,624,440 | 4/1997 | Huebner | 606/59 |

FOREIGN PATENT DOCUMENTS

| | | | |
|---|---|---|---|
| 0029298 A1 | 5/1981 | European Pat. Off. | A61B 17/18 |
| 9016227 U | 3/1991 | Germany | A61B 17/56 |
| 4421223 A1 | 12/1995 | Germany | A61B 17/60 |

OTHER PUBLICATIONS

Simply Versatile ACE–Fisher™ Wire Tension System, Ace Medical Company (undated).
Carbon MonOtube, External Fixation System, Howmedica ©1994, Howmedica Ind. Rutherford, NJ.
Torus External Fixation System, ©1993 Zimmer, Inc.
Ace Unifix External Fixation System (undated).
Fixano Product List, Fixateur A Anneaux, Ring Fixator (undated).
The AO/ASIF Hybrid Fixator, Technique Guide, ©Synthes (USA) 1992.
OrthoFrame™, OrthoLogic®, 2850 South 36th Street, Phoenix, Arizona (Feb. 1996).
Orthofix® Mudulsystem [EBI Medical Systems] (undated).
The Original Hoffmann External Fixation System, Howmedica (undated).

*Primary Examiner*—Michael Buiz
*Assistant Examiner*—David O. Reip
*Attorney, Agent, or Firm*—Larkin, Hoffman, Daly & Lindgren, Ltd.

[57] ABSTRACT

An external fixation system (10) comprising one or more rings (14), elongated members (16), extension fingers (18) with pin holders (52), wire holders (22), clamping assemblies (20), screws (24) or wire (26) for securing parts of a bone (12), and rod connectors (174). The extension fingers (18) are positioned axially and radially along the elongated members (16). The pin holders (52) move axially along and radially around the extension fingers (18), and are secured in place using a one-hand operation which also secures the screw (24) in place. The screws (24) are secured to the pin holders (52) from a point which may be positioned and oriented with full spatial articulation in three dimensions. The rings (14) are provided with openings (104) composed of intersecting apertures (106) to decrease the spacing between available locations. A lengthening-compression-distraction (LCD) bar (28) permits traction or compressive forces to be exerted on the bone (12), as well as dynamization for weight-bearing compression. Certain components of the LCD bar (28) can be reconfigured during fabrication to facilitate use in a transport mode. The rod connector (174) joins two elongated members 16 at a selected and adjustable angle, and includes two open-ended U-collars (176, 178) stacked on a shaft (182) for rotation until the U-collars (176, 178) are compressed to clamp the elongated members (16).

8 Claims, 13 Drawing Sheets

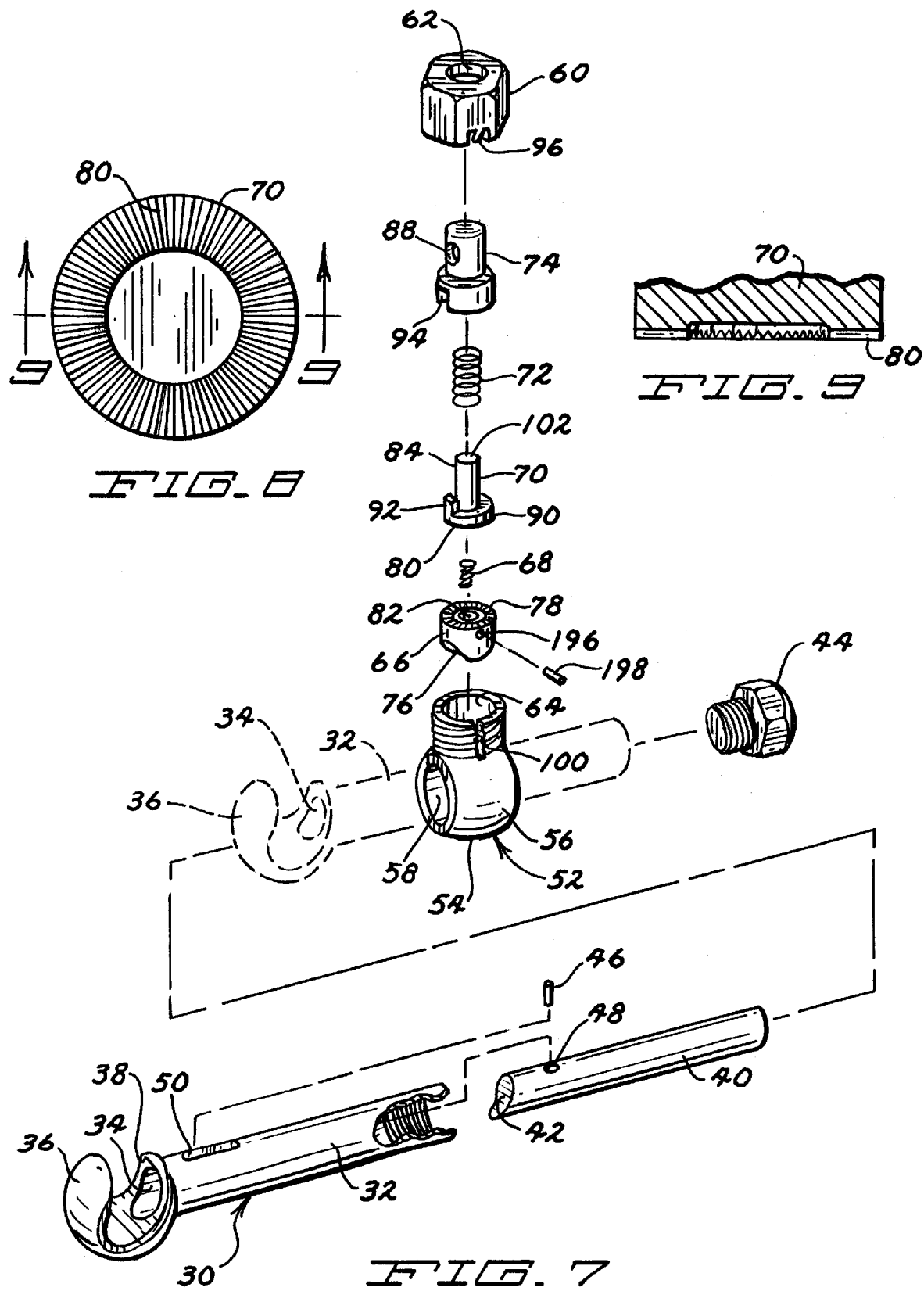

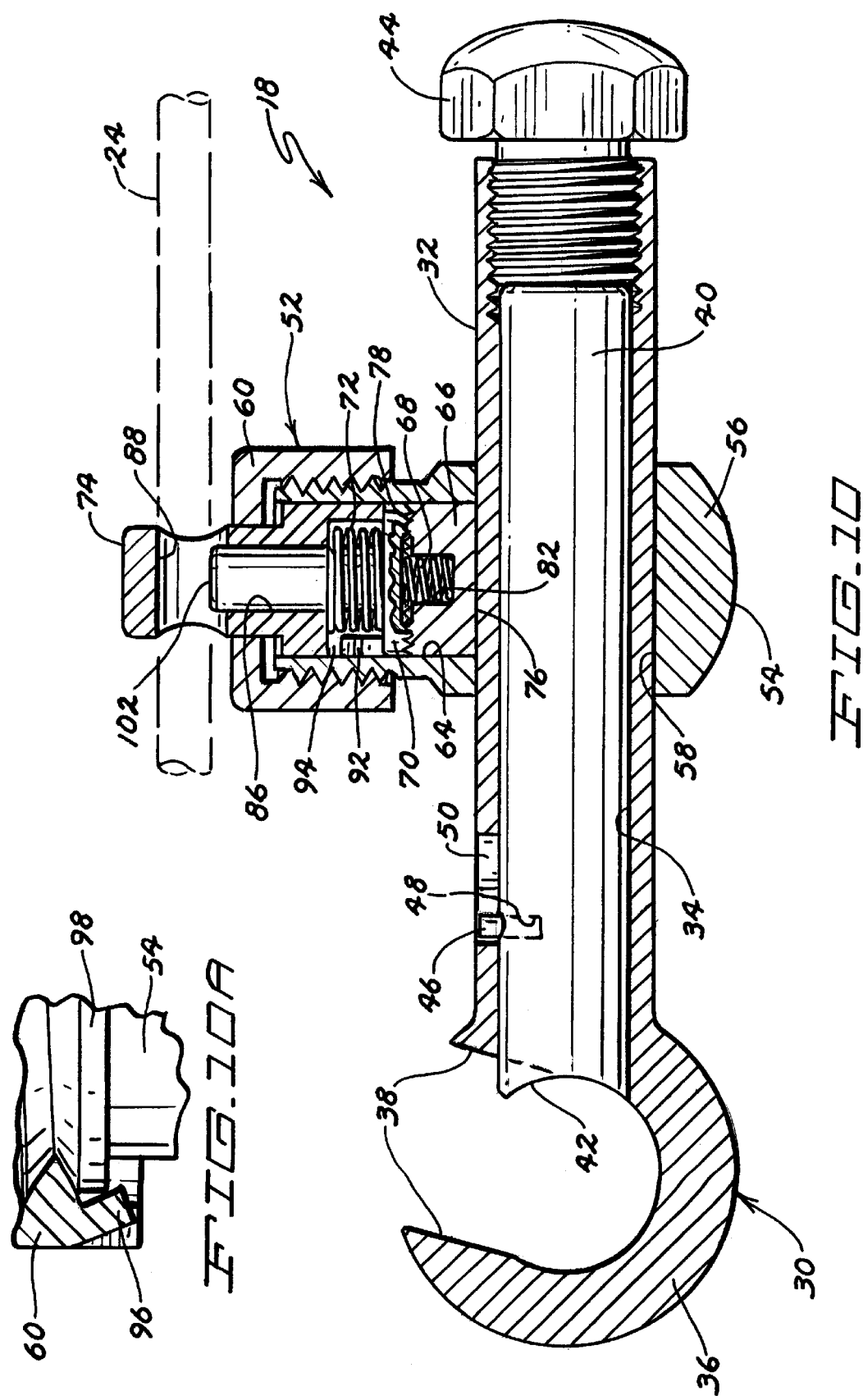

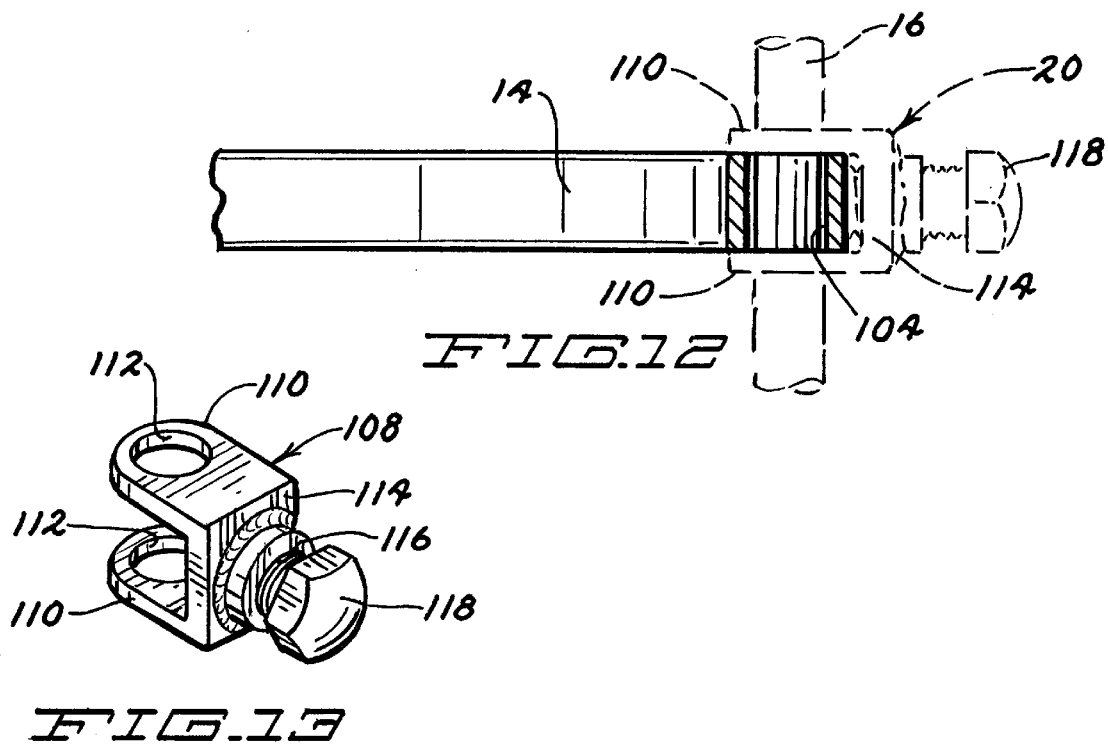
FIG.12
FIG.13
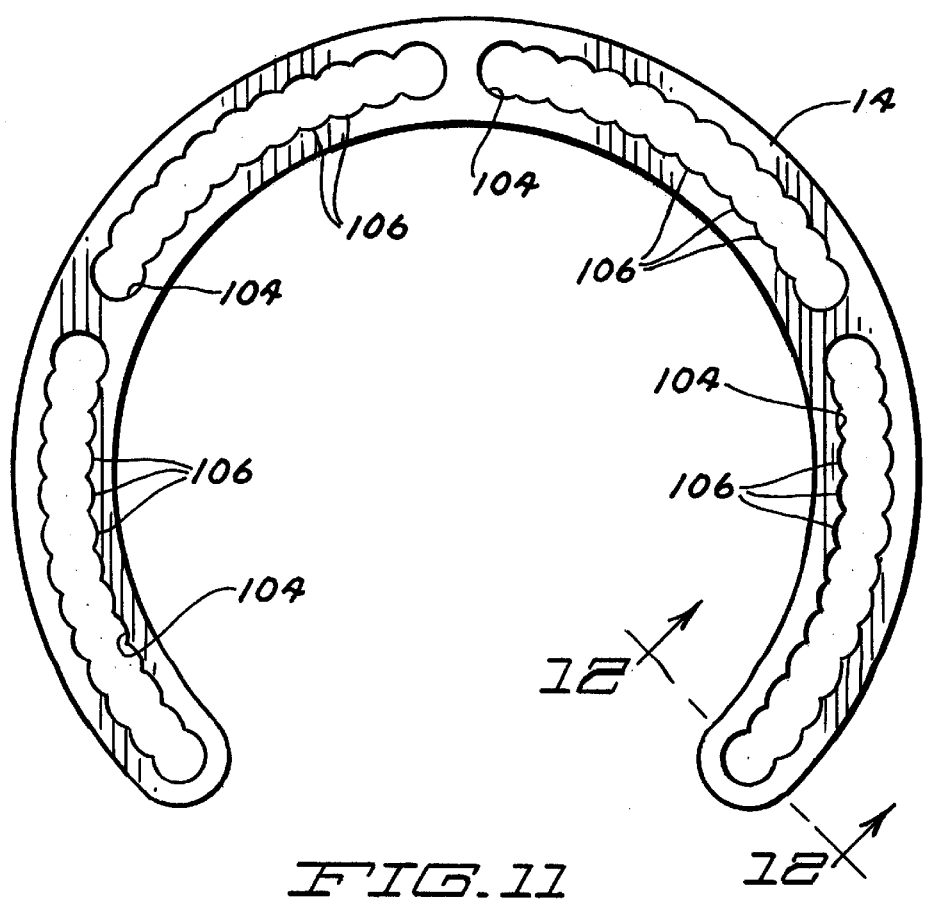
FIG.11

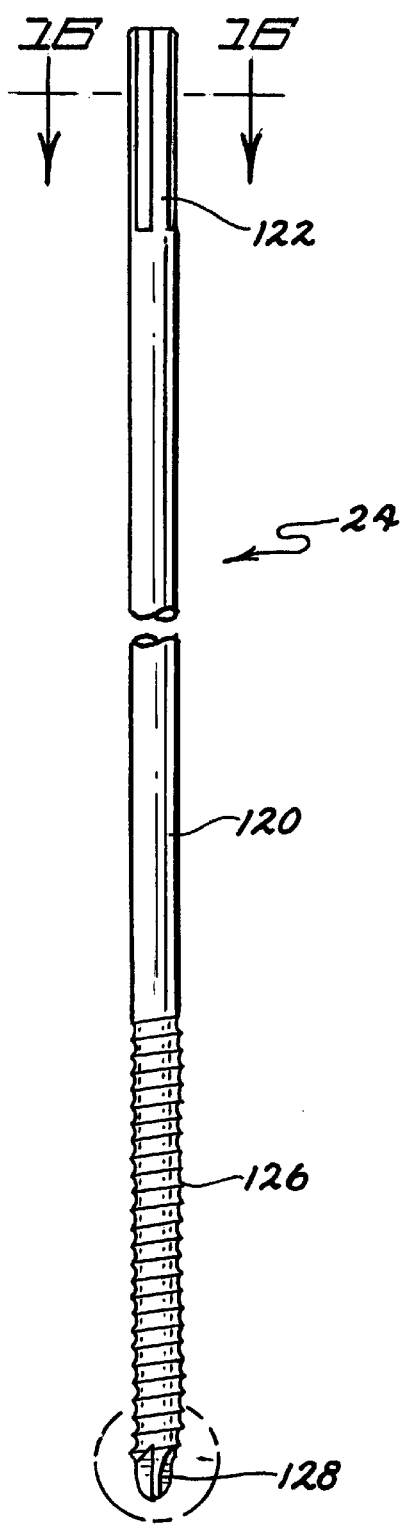
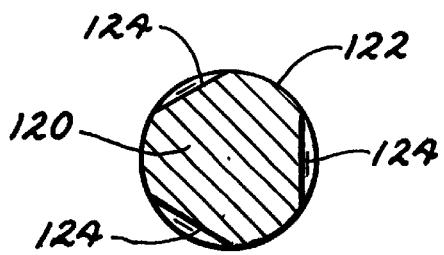
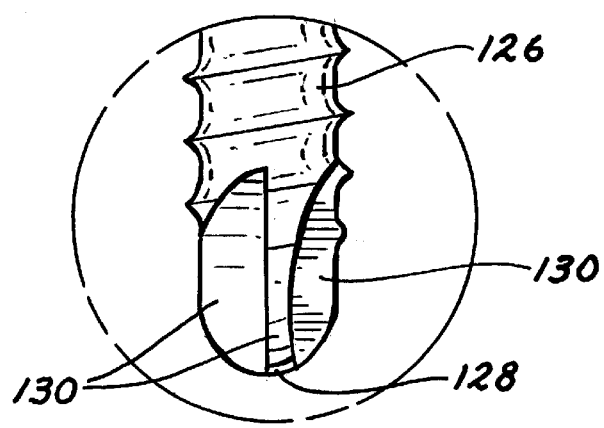
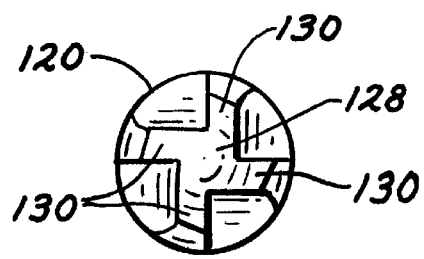
FIG.14
FIG.16
FIG.15
FIG.17

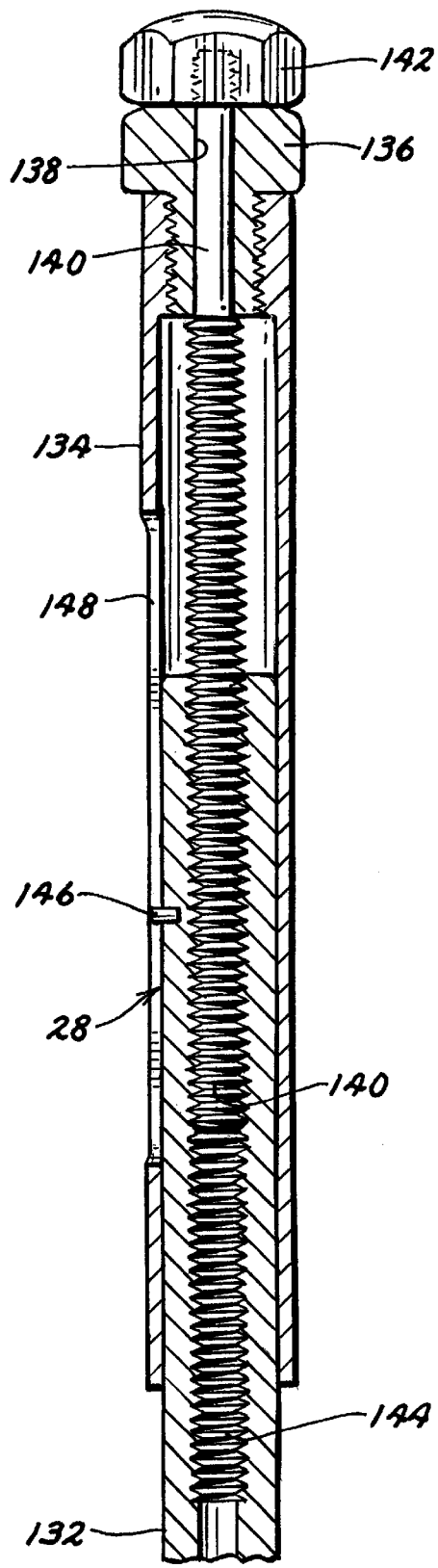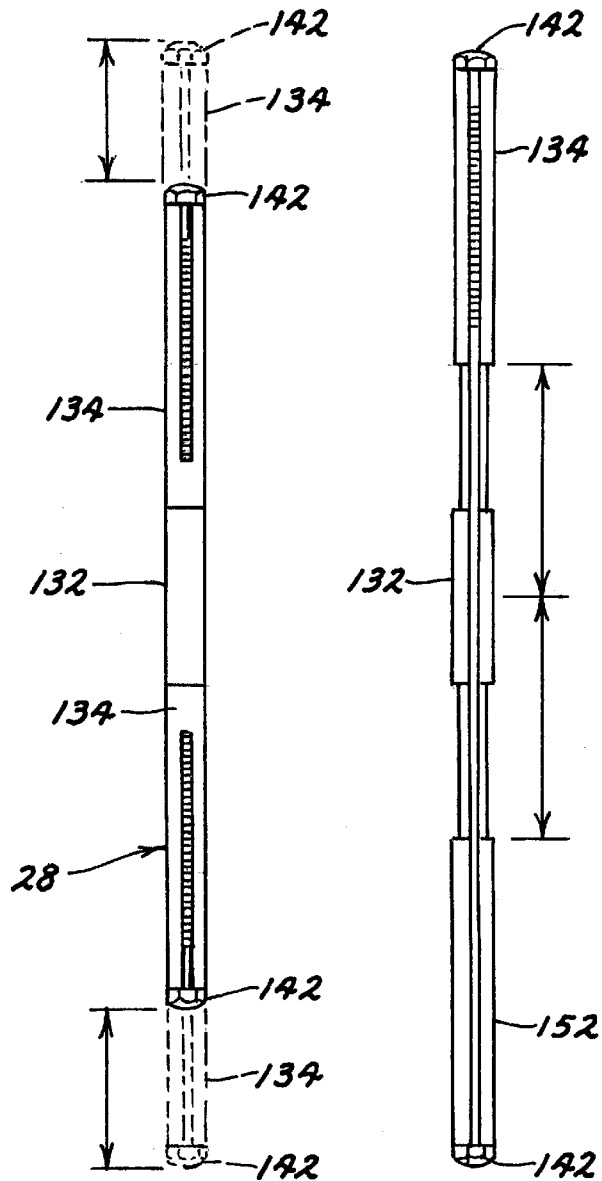
FIG.19
FIG.20
FIG.21

# ARTICULATED EXTERNAL ORTHOPEDIC FIXATION SYSTEM AND METHOD OF USE

This is a Divisional of co-pending Parent application Ser. No. 08/717,224, filed Sep. 26, 1996.

BACKGROUND OF THE INVENTION

1. Field of the Invention

The present invention relates generally to external fixation systems used for securing separated or fractured segments of a bone in proper position, alignment, and orientation for healing or therapeutic manipulation.

2. Scope of the Prior Art

A wide variety of external fixation or wire tensioning systems are known to the orthopedic field. Two popular types are the "ring-and-rod" and the "jointed bar" systems, and several variations or hybrids based upon these two basic types are known. The "ring-and-rod" systems are characterized by longitudinal bars having pin-holding clamps which can be secured in different positions and angular configurations relative to the parts of a fractured bone requiring fixation. The longitudinal bars may optionally be mounted on one or more partial rings which circumscribe the bone. In contrast, the "jointed bar" systems are composed of several rigid segments coupled by various types of joints which may be locked in a desired configuration.

Jointed bar systems generally display the advantage of providing a greater range or degree of non-uniform articulation, but inherently present a significantly larger profile and greater complexity in positively securing the segments and joints in the desired configuration. Ring-and-rod systems may provide greater stability and a lower lateral profile with the ability to employ both screw fixation and wire tensioning, however their range of articulation is generally more limited and the available locations for positioning the screws and wire relative to the corresponding rods or rings may be insufficient (or less than desirable) for some applications.

Among systems utilizing rings, there is a further distinction between "through-the-ring" systems and "outrigger" systems. In through-the-ring systems, the main longitudinal rods, bars, and wire or pin holders extend through apertures in the ring itself and are secured in position by fasteners or clamps. In "outrigger" systems, the rods are connected to the rings by clamps which ride along the peripheral edge or rim of the ring. The outrigger systems can provide continuous adjustability in the position of the rods along the rings, but lack the stability and usually present a larger lateral profile than through-the-ring systems.

Several representative examples of commercially-available external fixation systems which exemplify the "ring and rod" and "jointed bar" systems and their hybrids or variations are disclosed in the papers accompanying this specification, and are incorporated herein by reference as though fully set forth and described in detail, along with the additional patents and prior art references made of record.

SUMMARY OF THE INVENTION

The external orthopedic fixation system of this invention provides the operator with the advantages of the increased stability, full spatial articulation, and lower lateral profiles than previous ring-and-rod or jointed bar systems. In addition, the components of the system may be more readily positioned and secured to provide optimal placement and orientation of the pins, screws, or tensioning wires for the desired effect in the given application.

Briefly described, the external fixation system includes extension fingers which may be positioned both axially and radially along an elongated rod member, and pin holders which may be moved axially along and radially around the extension fingers. The extension fingers and pin holders may each be clamped and secured in a desired position using a one-hand operation. The point at which the screws or wire are mounted on the pin holders may be positioned and oriented with full spatial articulation in three dimensions. The partial rings are provided with openings to receive the elongated rod members (or wire holder members), with the openings composed of intersecting apertures to decrease the spacing between available locations for the elongated rod members or wire holders. One or more of the elongated rod members may constitute a lengthening-compression-distraction (LCD) bar which permits longitudinal forces to be exerted on segments of the bone, or may be easily converted to a dynamic mode allowing weight-bearing compression. The basic components of the LCD bar can be reconfigured during fabrication to facilitate use in a transport mode.

BRIEF DESCRIPTION OF THE DRAWINGS

FIG. 7 is an exploded perspective view of the extension finger assembly of FIG. 2;

FIG. 8 is a detail view of the bottom surface of the clamp rod shown in FIG. 7;

FIG. 9 is a side cross section view of the bottom surface of the clamp rod shown in FIG. 7 taken through line 9—9 in FIG. 8;

FIG. 10 is a partially broken away side cross section view of the extension finger assembly of FIG. 2 taken along the longitudinal axis thereof;

FIG. 10A is a side cross section detail view of the extension finger assembly of FIG. 2 taken through line 10A—10A in FIG. 2;

FIG. 11 is a top plan view of an illustrative example of a ring member of this invention;

FIG. 12 is a side cross section view of the ring member of FIG. 11 taken through line 12—12 in FIG. 11;

FIG. 13 is a rear perspective view of one embodiment of the clamping assembly of this invention;

FIG. 14 is a side elevation view of an orthopedic screw using with the external fixation system of this invention;

FIG. 15 is a detail view of the distal tip of the orthopedic screw of FIG. 14;

FIG. 16 is a cross section view of the proximal end of the orthopedic screw of FIG. 14 taken through line 16—16 in FIG. 14;

FIG. 17 is an end elevation view of the distal end of the orthopedic screw of FIG. 14;

FIG. 19 is a cross section view of the LCD bar of FIG. 18 taken through line 19—19 in FIG. 18;

FIG. 20 is a diagrammatic depiction of the LCD bar of FIG. 18 showing the sleeve members in their retracted position, and their extended position in phantom;

FIG. 21 is a diagrammatic depiction of a reconfigured embodiment of the components of the LCD bar in the transport mode;

DETAILED DESCRIPTION OF THE PREFERRED EMBODIMENTS

The external orthopedic fixation system and method of this invention are illustrated in FIGS. 1–31 and referenced generally therein by the numeral 10. The apparatus, method, and inventive elements or components thereof are generally referred to interchangeably in this specification as the fixation system 10 for convenience.

Figure 1:
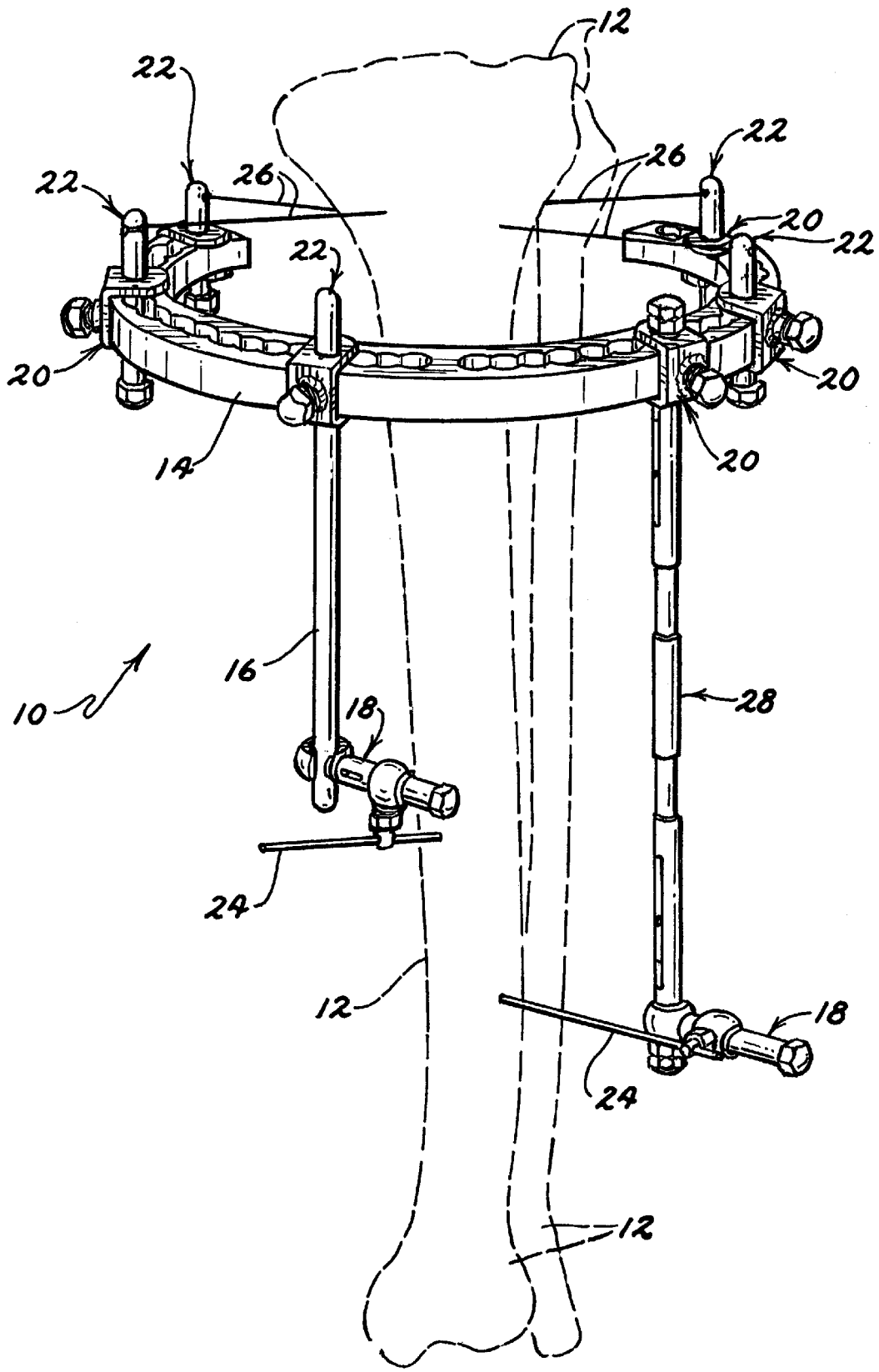
FIG. 1 is a front perspective view of one embodiment of each of the components of the external fixation system of this invention shown in a representative example of their applied environment.
Figure 5:
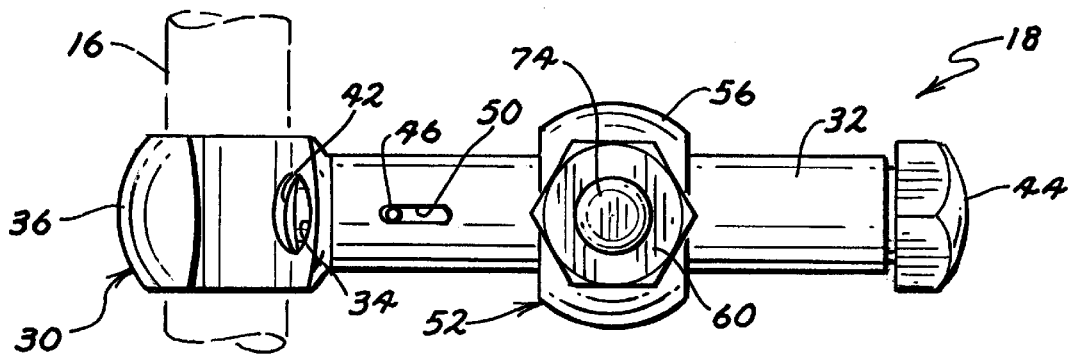
FIG. 5 is a top view of the extension finger assembly of FIG. 2.
Figure 3:
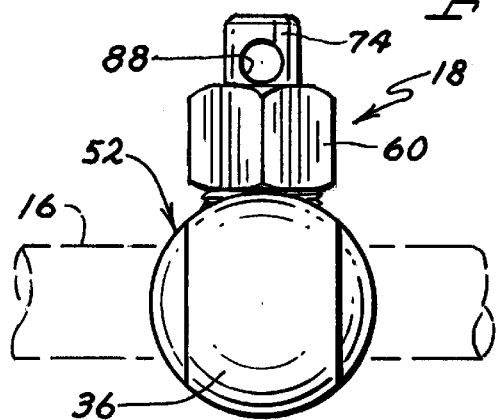
FIG. 3 is a left end elevation view of the extension finger assembly of FIG. 2.
Figure 4:
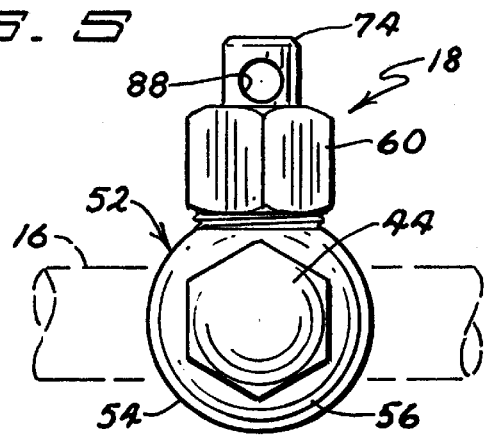
FIG. 4 is a right end elevation view of the extension finger assembly of FIG. 2.
Figure 2:
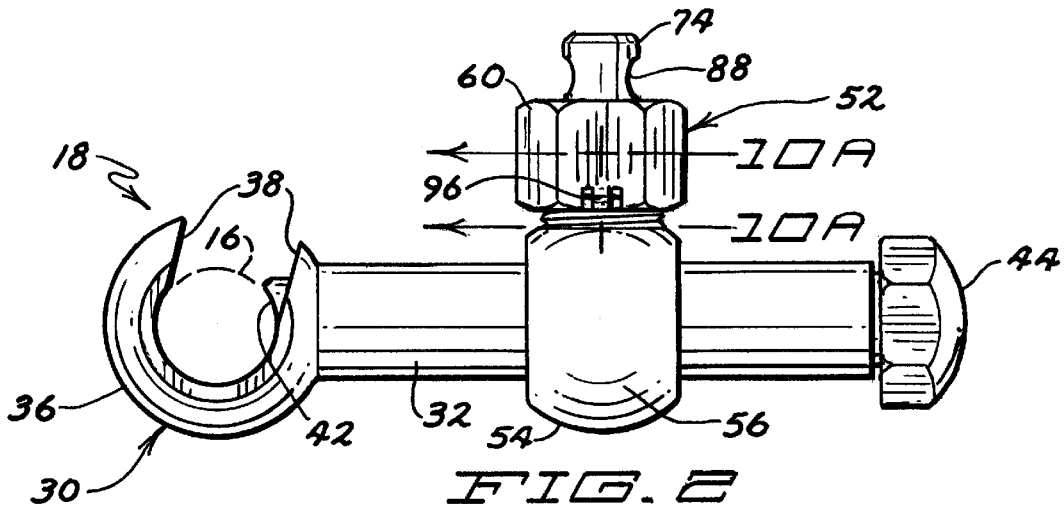
FIG. 2 is a side elevation view of one embodiment of the extension finger assembly of this invention.
Figure 6:
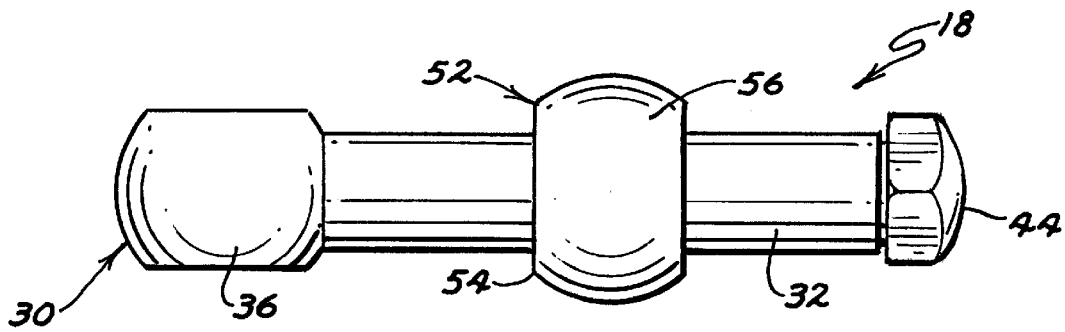
FIG. 6 is a bottom view of the extension finger assembly of FIG. 2.

Referring particularly to FIG. 1, the fixation system 10 includes several components utilized to secure the proper position, alignment, and orientation of a bone 12 during healing or for therapeutic manipulation, illustrative examples of those components being shown in a representative depiction of their applied environment wherein the bone 12 is the tibia in the leg of a patient.

The components of the fixation system 10 generally include one or more of the following: a ring member 14, an elongated rod 16, an extension finger assembly 18, a clamping assembly 20, a wire holder member 22, screws or pins 24, wire 26, and a lengthening-compression-distraction (LCD) bar 28 which may also be reconfigured for use in a transport mode as described in further detail below. It may be readily appreciated that any number of each component 14–28 may be utilized as needed or desired in a particular application, and that certain components 14–28 may be omitted entirely in particular applications.

Extension Finger Assembly (18)

Referring particularly to FIGS. 2–10, one embodiment of the extension finger assembly 18 and its constituent subcomponents are shown in greater detail. The extension finger assembly 18 includes a generally elongated body member 30 having a generally cylindrical sleeve section 32 defining a longitudinal bore 34 extending therethrough. An open C-shaped semicircular engagement collar 36 is disposed at and extends fixedly from one end of the sleeve section 32, the collar 36 and sleeve section 32 having generally parallel faces 38 defining an opening sized to receive a portion of the elongated member 16 therethrough. The bore 34 receives a push rod 40 in close sliding contact therein, the push rod 40 having a length slightly less than that of the bore 34 of the sleeve section 32. The end of the push rod 40 disposed toward the collar 36 extends from the bore 34 of the sleeve section 32 into the interior region encompassed by the collar 36 and defines a generally concave face 42 having a diameter conforming to the surface of the elongated member 16 received within the interior region of the collar 36. The opposing end of the push rod 40 abuttingly contacts the inner surface of a securing member 44 threadedly engaged within the end of the sleeve section 32, the securing member 44 urging the concave surface 42 of the push rod 40 into frictional engaging contact with the elongated member 16 to mount and secure the body member 30 on the elongated member 16 at a selected position and in a desired orientation. An alignment pin 46 is received within an aperture 48 in the push rod 40, and extends radially outward from the push rod 40 and is slidably received within an exposed channel 50 extending longitudinally along the sleeve section 32 to maintain the concave face 42 of the push rod 40 in the proper orientation and alignment for engaging the surface of the elongated member 16, and to prevent the push rod 40 from rotating and obstructing the interior region of the collar 36.

A pin holder assembly 52 is mounted on the body member 30 so as to slide axially along the exterior surface of the sleeve section 32 and rotate completely around the sleeve section 32. The pin holder assembly 52 includes an eye-bolt or body member 54 having an enclosed collar 56 at one end, the collar defining a bore 58 sized to slidably receive the sleeve section 32 therethrough in close frictional contact. The opposing end of the body member 54 is threaded to receive a securing member 60 thereon, the securing member 60 defining a central aperture 62 extending therethrough. The body member 54 similarly defines a hollow bore 64 into which a clamp member 66 is received, followed in linear sequence by a first compression spring 68, clamp rod 70, second compression spring 72, and stem 74. The bottom face 76 of the clamp member 66 is generally concave, having a diameter conforming to the exterior surface of the sleeve section 32. The top face 78 of the clamp member 66 defines a multiplicity of radial serrations or teeth which mesh or mate with a similar multiplicity of radial serrations or teeth defined by the bottom face 80 of the clamp rod 70. The first compression spring 68 is received within a closed bore 82 extending into the top face 78 of the clamp member 66, to contact and exert pressure biasing the clamp rod 70 and clamp member 66 away from one another. The serrations are sufficiently shallow or beveled so that the clamp rod 70 and clamp member 66 may rotate relative to one another through a continuous series of indexing positions when the clamp rod 70 and clamp member 66 lightly or incidentally contact one another, but engage and secure the clamp rod 70 and clamp member 66 relative to one another against rotation when the force exerted on the clamp rod 70 by the second compression spring 72 and stem 74 exceed the spring force of the first compression spring 68 and the clamp rod 70 and clamp member 66 are pressed into engaging contact. The second compression spring 72 is received on a top barrel portion 84 of the clamp rod 70, and the top barrel portion 84 of the clamp rod 70 is received within a bore 86 defined by the stem 74. The top portion of the stem 74 extends through the aperture 62 in the securing member 60, and defines a pin-receiving bore 88 extending therethrough and having a longitudinal axis aligned generally parallel with that of the sleeve section 32. The lower radial flange 90 of the clamp rod 70 defines an upwardly-extending projection 92 which is received within a mating slot or groove 94 defined by the wall of the stem 74, such that the stem 74 will not rotate relative to the clamp rod 70 at any time, and will not rotate relative to the clamp member 66 or sleeve section 32 of the elongated body member 30 when the serrations or teeth of the clamp rod 70 are pressed into engaging contact with those of the clamp member 66. The bore 86 in the stem 74 which receives the barrel portion 84 of the clamp rod 70 communicates with the pin-receiving bore 88 extending through the stem 74 so that the top end of the barrel portion 84 of the clamp rod 70 extends into the pin-receiving bore 88.

The pin holder assembly 52 is fabricated and mounted on the sleeve section 32 over the threaded end thereof prior to the securing member 44 being attached to the sleeve section 32. The pin holder assembly 52 is then assembled with the securing member 60 being threaded onto the body member 54, and one or a pair of clinch tabs 96 are bent inwardly to engage under the radial flange 98 disposed beneath the threaded region to prevent removal of the securing member 60 from the body member 54, yet permit the securing member 60 to be rotated relative to the body member 54 along the threaded region to tighten and loosen the clamping pressure exerted sequentially against the stem member 74, clamp rod 70, clamp member 66, and sleeve section 32.

The clamp member 66 further defines an aperture 196 receiving an alignment and stopping pin 198 extending laterally therefrom. The pin 198 is slidably received within a slot 100 defined by the threaded neck region of the pin holder assembly 52, to thereby retain the concave face 76 of the clamp member 66 in proper orientation and prevent the clamp member 66 from dropping out of the pin holder assembly 52 into the bore 58 when the sleeve 32 is not present.

It may be readily appreciated that the extension finger assembly 18 may be mounted on an elongated member 16 and moved to a desired position and orientation, with the securing member 44 being rotated to apply pressure on the push rod 40 and urge the concave face 42 of the push rod 40 into contact with the elongated member 16. The securing member 44 is further tightened to clamp or secure the body member 30 at that desired position and orientation to prevent the body member 30 from sliding or rotating relative to the elongated member 16, or the securing member 44 may be loosened slightly to selectively permit such axial or rotational adjustment of the body member 30 relative to the elongated member 16.

Similarly, when a pin or screw 24 is received within the pin-receiving bore 88 of the stem 74, the screw 24 and stem 74 may rotate substantially freely with the screw 24 being maintained in a plane generally parallel to the plane of the longitudinal axis of the sleeve section 32. When the securing member 60 is initially tightened on the body member 54, the clamp rod 70 will be urged into slight contact with the clamp member 66 and opposed by the force of the first compression spring 68, thus permitting the stem 74 and screw 24 to rotate in an indexing manner relative to the sleeve section 32 and clamp member 66, causing the pin holder assembly 52 to emit an audible clicking or ratcheting noise. When the securing member 60 is further tightened onto the body member 54, the clamp member 66 is urged into engaging contact with the sleeve section 32 to securely fasten the sleeve section 32 between the clamp member 66 and opposed confronting surface of the collar 56. The serrated or toothed faces 78, 80 of the clamp rod 70 and clamp member 66 are pressed into engaging contact with one another, and the top surface 102 of the clamp rod 70 is urged into engaging contact with the screw 24 to securely fasten the screw 24 between the top surface of the clamp rod 70 and the opposed confronting surface of the stem 74. Thus, tightening the securing member 60 simultaneously prevents the pin holder assembly 52 from sliding axially or rotating relative to the elongated body member 30, prevents the stem 74 and screw 24 from rotating relative to both the pin holder assembly 52 and the elongated body member 30, and prevents the screw 24 from sliding axially within the bore 88 relative to the stem 74 and the pin holder assembly 52.

Ring Member (14)

Referring particularly to FIGS. 11 and 12, an illustrative embodiment of a ring member 14 and corresponding clamping assembly 20 are shown in greater detail. As shown in FIG. 11, the ring member 14 is an integral semicircular open torpid having an inner, central, and outer diameters, a radial thickness, and which circumscribes an arc between the radiused free ends thereof. The ring member has a uniform thickness as shown in FIG. 12. The ring member 14 defines four openings 104, each composed of a plurality of intersecting apertures 106 or placeholders through which an elongated member 16 may be slidably received.

In one preferred embodiment of the ring member 14, the inner diameter is 6.300", the central diameter is 7.111", the radial thickness is 0.812", the outer diameter is 7.112", and the thickness is 0.625". The ring member 14 extends through an arc of approximately 280°. In that first embodiment, the two openings 104 adjacent to the free ends each contain twelve apertures or placeholders, and the two intermediate openings 104 each contain eleven apertures or placeholders, for a total of forty-six apertures 106 defining four openings 104. Each aperture 106 has a diameter of approximately 0.500", and the centerpoints of adjacent apertures 106 in each opening 104 are spaced apart approximately 5°. Each opening 104 is spaced apart 12° from the adjacent openings 104 measured through the centerpoints of the corresponding end apertures 106.

In a second preferred embodiment of the ring member 14, the inner diameter is 7.480", the central diameter is 8.292", the radial thickness is 0.812", the outer diameter is 9.104", and the thickness remains 0.625". The ring member 14 similarly extends through an arc of approximately 280°. In that second embodiment, the two openings 104 adjacent to the free ends each contain thirteen apertures or placeholders, and the two intermediate openings 104 each contain sixteen apertures or placeholders, for a total of fifty-six apertures 106 defining four openings 104. Each aperture 106 has a diameter of approximately 0.500", and the centerpoints of adjacent apertures 106 in each opening 104 are spaced apart approximately 4°. Each opening 104 is similarly spaced apart 12° from the adjacent openings 104 measured through the centerpoints of the corresponding end apertures 106.

While the particular dimensions of these representative embodiments of the ring member 14 are provided purely for exemplary purposes in order to facilitate an understanding of the relative proportions of the ring member 14 compared to the bone 12 and anticipated working environment, and in particular the degree of freedom in selecting the optimal available placement and spacing for the elongated members 16 or wire holders 22 along the ring member 14, it may be readily appreciated that a wide variety of dimensions and tolerances may be selected for other embodiments of the ring member 14 as dictated by the needs of the working environment and the particular application, the stresses placed upon the ring member 14 in a particular application, as well as the desires of the operator.

Clamping Assembly (20)

Referring to FIGS. 12 and 13, each clamping assembly 20 includes a U-shaped body 108 having a pair of parallel legs 110 each defining a radiused end and an aperture 112 extending therethrough, with a bridge section 114 connecting the pair of legs 110 and defining a threaded aperture 116 through which a bolt 118 is received, the distal tip of the bolt 118 extending through the opposing face of the bridge section 114 and into the region between the legs 110. The legs 110 are spaced apart slightly greater than the uniform thickness of the ring member 14 so that the clamping assembly 20 is slidably mounted on the ring member 14 to ride along the arc of the ring member 14 on the exterior side thereof to align the apertures 112 in the legs 110 with the apertures 106 defining the openings 104. The distal tip of the bolt 118 contacts the exterior surface of the ring member 14 when the bolt 118 is tightened within the threaded aperture 116. An elongated member 16 (or wire holder 22) is inserted through the aperture 112 in one leg 110, through the desired aperture 106 or placeholder in an opening 104 of the ring member 14, and through the aperture 112 in the opposing leg 110. As the bolt 118 is tightened into contact with the exterior surface of the ring member 14, the bridge section 114 and legs 110 of the clamping assembly 20 are pulled radially outward relative to the ring member 14 and into contact with the elongated member 16 (or wire holder 22), which is in turn pressed radially outward into contact with the wall of the ring member 14. The elongated member 16 (or wire holder 22) is thereby securely fastened in position relative to the ring member 14 such that the elongated member 16 (or wire holder 22) cannot slide longitudinally relative to the ring member 14, and the elongated member 16 (or wire holder 22) remains at a fixed position along the arc of the ring member 14 due to both the engaging contact and the undulating or curved inner wall of the opening 104 formed by the plurality of intersecting apertures 106.

Pin or Screw (24)

Referring particularly to FIGS. 14–17, a representative embodiment of a pin or screw 24 used with the external fixation system 10 is shown, the screw 24 having a generally cylindrical shaft 120, a proximal end 122 defining a plurality of semi-hexagonal facets 124 designed to mate with a drill or manual tool for imparting rotation to the screw 24, a distal end 126 having a region of helical threads and a boring or cutting tip 128 having four blades 130 designed to penetrate the bone 12 and form a bore hole, clear debris from the bore hole, and pull the screw 24 securely into the bone 12.

Lengthening-Compression-Distraction Bar (28)

Figure 18:
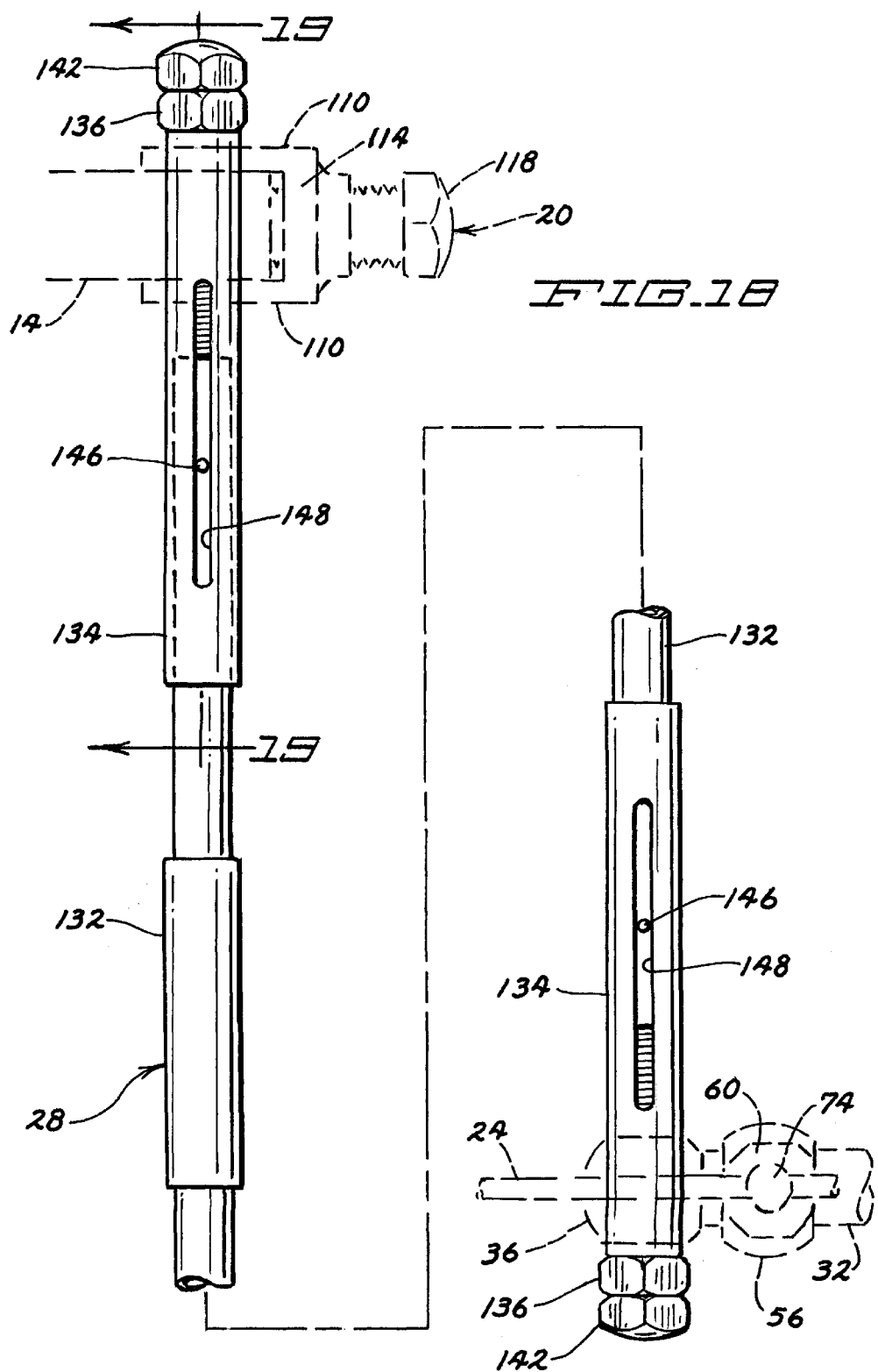
FIG. 18 is a side elevation view of one embodiment of the lengthening-compression-distraction (LCD) bar of this invention with a ring member mounted at one end and an extension finger assembly at the opposing end.

Referring particularly to FIGS. 18–21, 27, and 28, a representative embodiment of the lengthening-compression-distraction bar 28 (or "LCD" bar 28) is shown in detail. A first embodiment of the LCD bar 28 is shown in FIGS. 18 and 19, in which the LCD bar 28 includes a generally cylindrical central segment 132 having a pair of hollow, adjustable sleeve members 134 each disposed on opposing ends thereof, the open ends of each sleeve member 134 being sealed by a threaded end cap 136 fixedly received within a threaded region of the bore extending through the sleeve member 134. Each end cap 136 defines a generally smooth cylindrical bore 138 through which a generally smooth region of a cylindrical shaft 140 extends. The outward end of each shaft 140 has a bolt head 142 fixedly threaded thereon, and the inward end of the shaft 140 threadedly engages within the corresponding open end of the hollow central segment 132 which has an interior bore 144 which is similarly threaded.

A pin 146 extends radially outward from an aperture defined by the exterior surface of the central segment 132 and is received within a slot or channel 148 defined by the adjustable sleeve member 134 to prevent the sleeve member 134 from rotating relative to the central segment 132.

Figure 27:
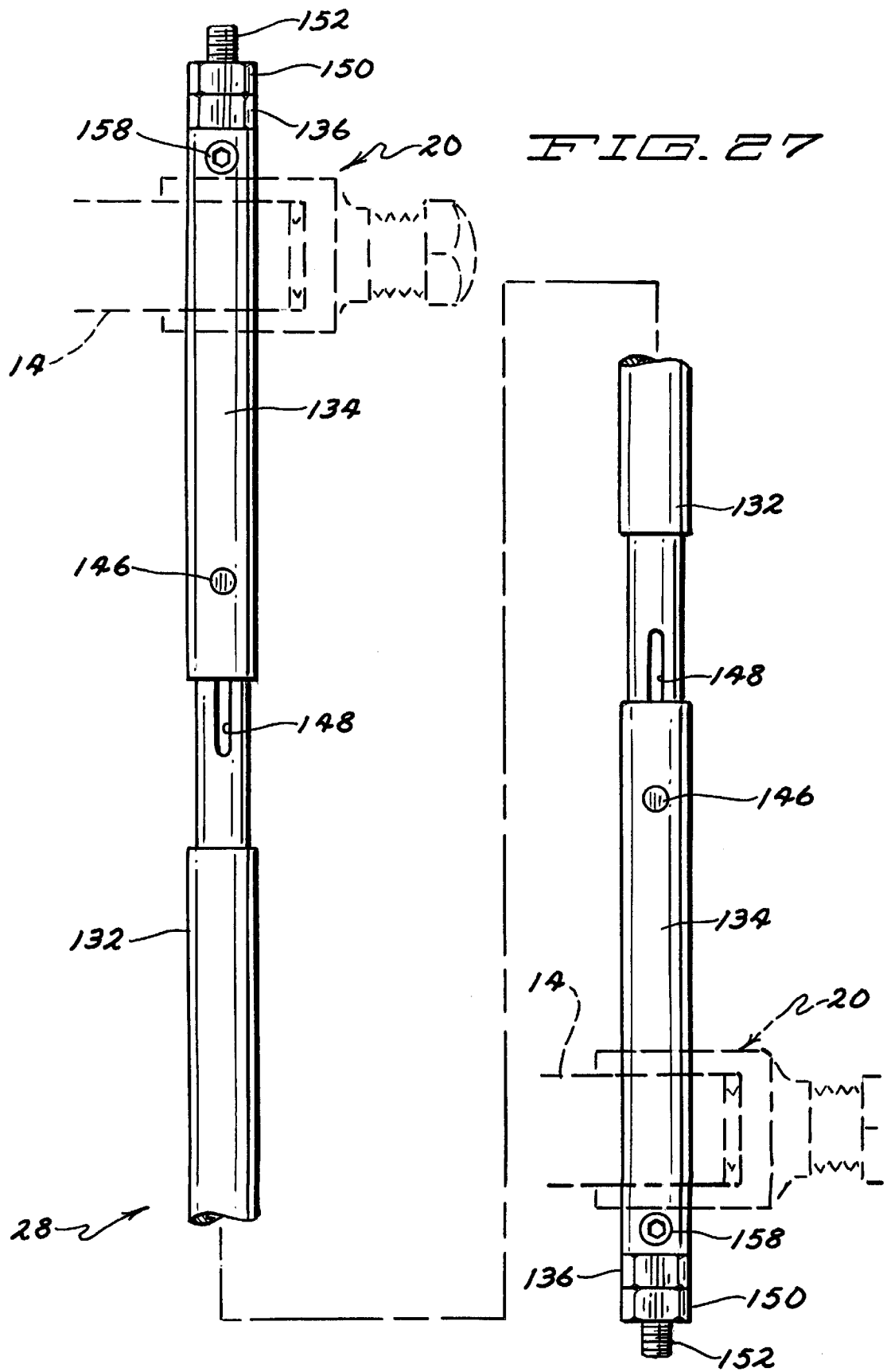
FIG. 27 is a side elevation view of the LCD bar with ring members mounted at each opposing end.
Figure 28:
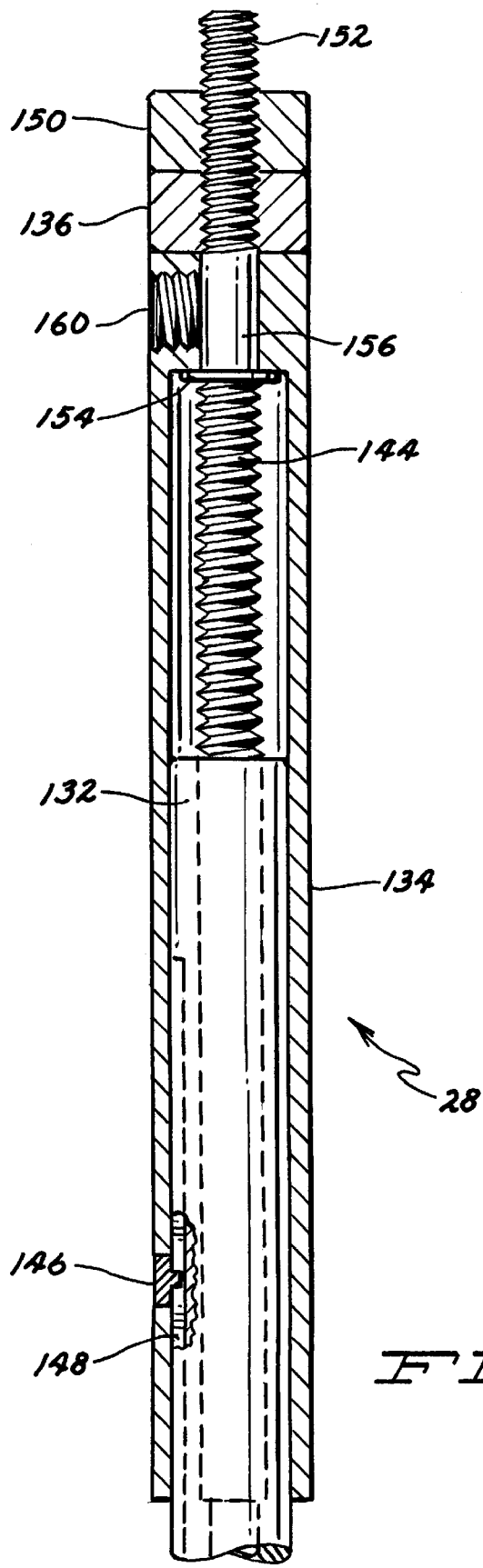
FIG. 28 is a partially broken away cross section view of the LCD bar of FIG. 27 taken through line 28—28 in FIG. 27.
Figure 29:
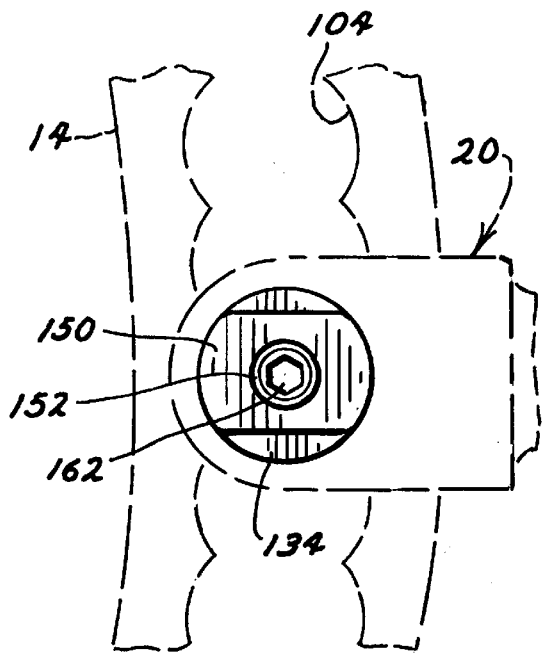
FIG. 29 is an end view of the LCD bar received within a ring member and clamp.

In a second embodiment of the LCD bar 28 shown in FIGS. 27–29, a threaded nut 150 replaces the bolt head 142, with the threaded nut 150 and the end cap 136 both being received on a corresponding threaded region 152 extending longitudinally from and fixedly connected to the end of the central segment 132. In this second embodiment, the orientation of the pin 146 and slot 148 are reversed, so that the pin is frictionally engaged in the sleeve 134 and extends into a slot 148 defined in the central segment 132, a construction which increases the strength of the embodiment. A washer 154 is disposed between the inner surface of the sleeve member 134 and confronting surface of the central segment 132 to facilitate rotation of the two components relative to one another without freezing or undue friction. The extending region 152 further defines a generally smooth intermediate surface 156 against which a hex screw 158 may be tightened to prevent rotation of the sleeve member 134 relative to the central segment 132, the hex screw 158 being received within a transverse threaded aperture 160 extending entirely through the wall of the sleeve member 134. Referring to FIG. 29, the end of the extension region 152 defines a hex slot 162 depending axially into the extension region 152 and aligned with the longitudinal axis, and designed to receive a hex key (not shown) of the same size as that received by the hex screw 158. As may also be seen in FIG. 29, the threaded nuts 150 have a generally bi-truncated cylindrical shape defining a pair of opposing parallel sides.

In both embodiments of the LCD bar 28, the central segment 132 and the sleeve members 134 each have external cylindrical surfaces sized and shaped so as to be received within the C-shaped channel 36 of the extension finger members 18, so that one or more of the extension finger members 18 may be secured thereto in a similar manner as to an elongated member 16. Rotating the nut 142 or bolt 150 at the end of the LCD bar 28 will move the corresponding adjustable sleeve member 134 and any extension finger members 18 attached thereto longitudinally along the LCD bar 28 toward or away from its midpoint as shown in FIG. 20, to thereby place compressive or traction forces on the segments of bone 12 to which the extension finger members 18 are connected via screws 24 or wire 26 as shown in FIG. 1 and the lower portion of FIG. 18.

In addition, the LCD bar 28 (referring to the second embodiment as exemplary) may be "dynamized" or adapted for dynamic compression (for example, during the end stages of a fracture healing) by loosening both the threaded nut 150 and the end cap 136 several millimeters, so that the sleeves 134 are free to "float" that small distance relative to the central segment 132 when weight or tension is placed on the affected limb or bone 12, while the fixation system 10 continues to constrain or prevent any twisting or torquing of the limb and bone 12.

The patient may also be instructed to perform periodic tensioning or compression by placing the hex key into the hex screw 158, loosening the pressure exerted on the intermediate surface 156 of the extension region 152 to permit rotation thereof, inserting the hex key into the axial slot 162 and rotating the central segment 132 to lengthen or shorten the LCD bar 28, and retighten the hex screw 158 against the intermediate surface 156 to prevent inadvertent rotation of the central segment 132 relative to the sleeve members 134.

As shown in FIG. 21, the components of the LCD bar 28 may also be reconfigured during fabrication for use in a transport mode, in which the cylindrical shaft 140 extends completely through or along the central member 132 (to a point disposed on the lower end in FIG. 21) and engages both bolt heads 142 (in the first embodiment) or threaded nuts 150 (in the second embodiment), so that rotation in either the clockwise or counter-clockwise directions will move the central segment 132 longitudinally back and forth relative to the sleeve members 134, without affecting the longitudinal spacing between the sleeve members 134 and the corresponding extension fingers 18 and screw pins 22 attached to those sleeve members 134. In this manner, a section of the bone 12 may be secured to the central segment using one or more extension fingers 18 and screw pins 24 (or wire 26), and "transported" longitudinally relative to the segments of the bone 12 secured to the sleeve members 134.

Wire Holder (22)

Figure 23:
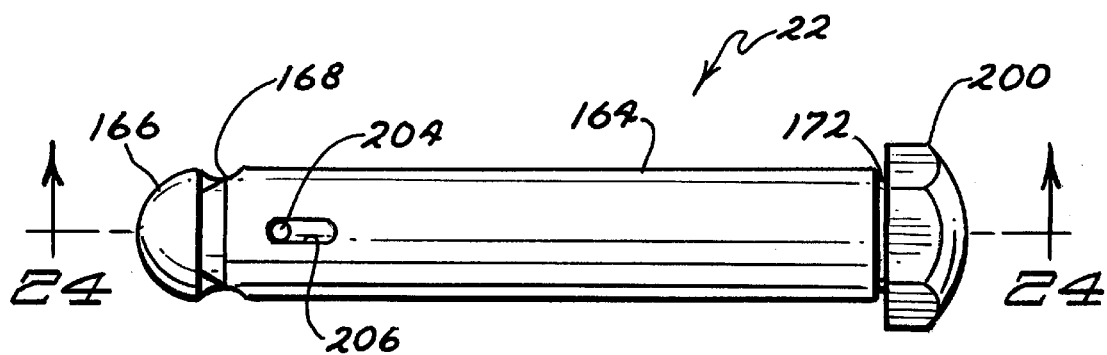
FIG. 23 is a bottom view of the wire holder of FIG. 22.
Figure 22:
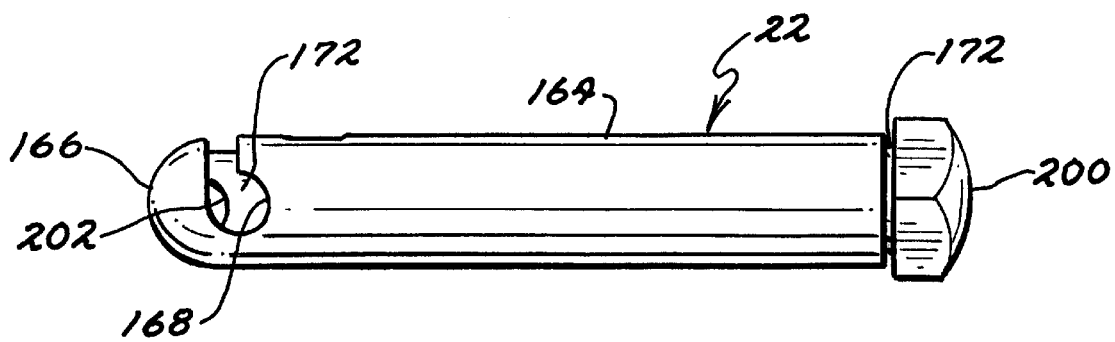
FIG. 22 is a side elevation view of the wire holder of FIG. 1.
Figure 24:
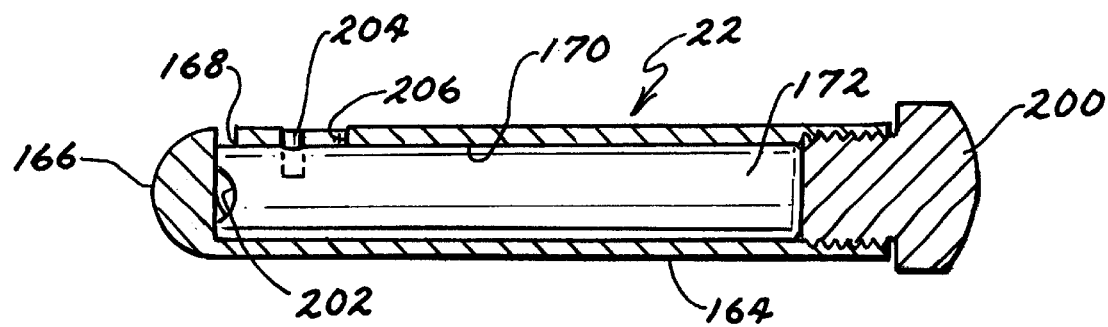
FIG. 24 is a side cross section view of the wire holder of FIG. 22 taken through line 24—24 in FIG. 23.

Referring to FIGS. 22–24, it may be seen that the wire holders 22 each include a generally cylindrical body segment 164 having a radiused tip 166 and defining a partially enclosed aperture 168 extending transversely therethrough. The body segment 164 defines a longitudinal bore 170 within which a plunger member 172 is slidably received, and which abuttingly contacts a threaded end cap 200 which is threadedly received within the open end of the body segment 164 opposing the radiused tip 166. The plunger member 164 further defines a transverse aperture or concave surface 202 which may be aligned with the boundary of the partially enclosed aperture 160 in the body segment 164, with the plunger member 172 being advanced into the body segment 164 by tightening the end cap 200 to securely pinch and hold any segment of wire 26 or a screw pin 24 which is placed within the aperture 168. The proper orientation of the plunger member 172 relative to the body segment 164 is similarly maintained using a pin 204 and slot 206 assembly similar to that previously described above in reference to other components.

Rod Connector (174)

Figure 25:
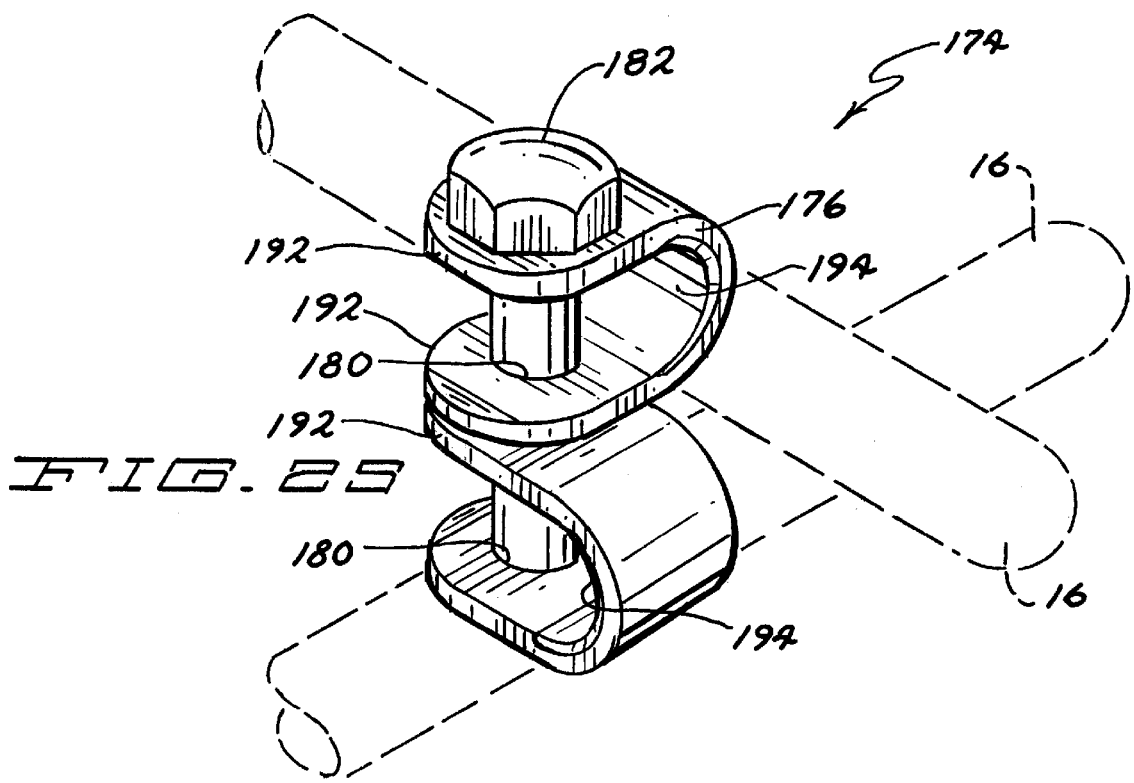
FIG. 25 is a perspective view of a rod connector used with the external fixation system of FIG. 1.
Figure 26:
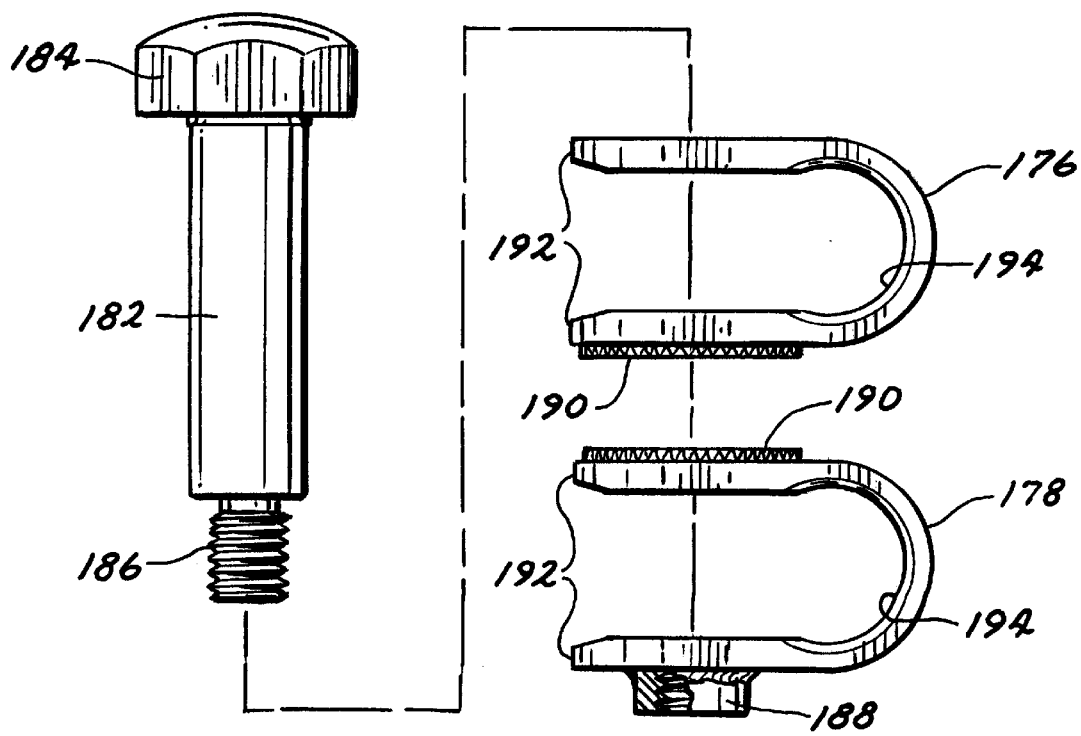
FIG. 26 is an exploded view of the rod connector of FIG. 25.

Referring to FIGS. 25 and 26, an additional component of the external fixation system is shown for joining two or more elongated members 16 at variable angles relative to one another, referred to herein as a rod connector 174. One of the primary uses of the rod connector 174 is to assemble a half-hexagonal U-shaped fixation frame for the pelvis as is known in the art, using three elongated members 16 joined by two rod connectors 174. It is understood that the rod connector 174 may be employed in other applications where two or more elongated members 16 are joined at acute or obtuse angles relative to one another.

The rod connector 174 consists of a first open-ended U-collar 176 and a second open-ended U-collar 178 stacked on top of each other, each U-collar 176, 178 defining aligned a pair of apertures 180 through which a bolt 182 is received to enclose the open ends of the both U-collars 176, 178 and permit the U-collars 176, 178 to rotate about the longitudinal axis of the bolt 182. The bolt 182 includes a faceted head 184 and a threaded tip 186 which is received within a matingly threaded neck region 188 on the bottom or outer side of the second U-collar 178. Each U-collar includes a toothed or serrated face 190 which closely confront and contact one another when the bolt 182 is tightened into the threaded neck region 188 to compress the U-collars 176, 178 toward one other.

When the bolt 182 is tightened into the threaded neck region 188 to compress the U-collars 176, 178 toward one other, the U-collars 176, 178 deform sufficiently such that the opposing legs 192 of the U-collars 176, 178 flex toward one another to reduce the inner diameter of the semi-circular clamping surface 194, thus contacting and exerting pressure on the portions of the elongated members 16 received within the semi-circular clamping surfaces 194 to secure and engage the elongated members 16 against rotation or axial movement within the U-shaped collars 176, 178. Angular movement of the elongated members 16 relative to one another is similarly restrained by the effect of the mating serrated faces 190.

Referring again to FIG. 1, one exemplary configuration is depicted in which a ring 14 is fixed or secured relative to the proximal end of a bone 12 by wires 26 extending from a plurality of wire holders 22 mounted in the openings 104 of the ring 14 using clamp assemblies 20, and intermediate or distal portions of the bone 12 are fixed or secured by screw pins 24 mounted in extension finger assemblies 18 carried at the ends of an elongated member 16 and LCD bar 28, respectively.

Figure 30:
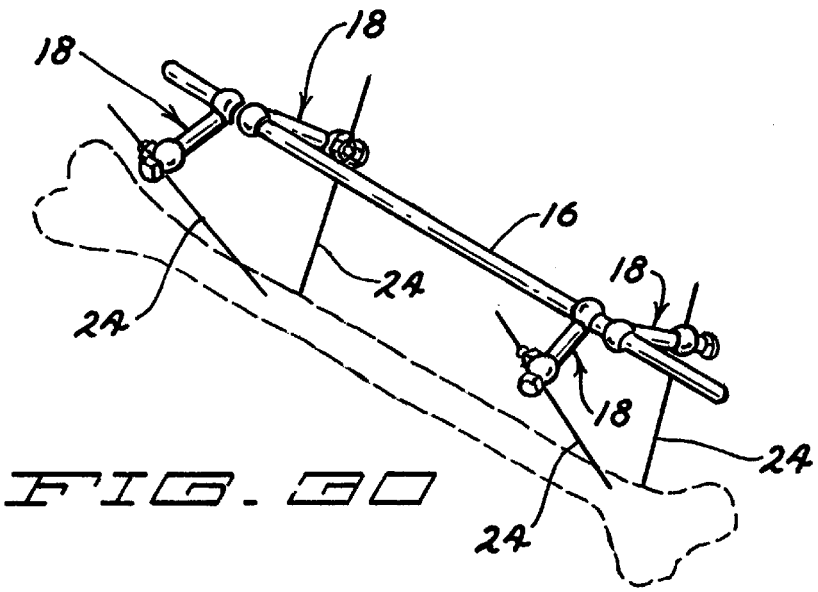
FIG. 30 is a diagrammatic view of one exemplary embodiment of the external fixation system in a working environment with four extension finger members and pins fixing a bone.
Figure 31:
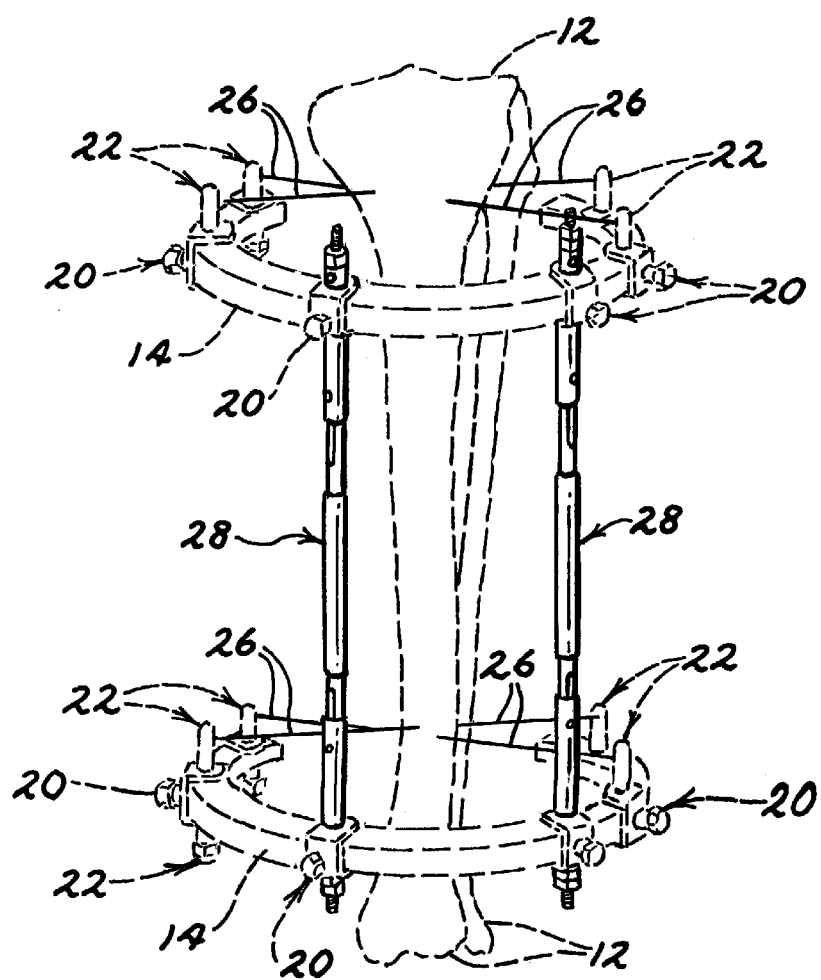
FIG. 31 is a diagrammatic view of one exemplary embodiment of the external fixation system in a working environment with two ring members connected by a pair of LCD bars, each with four wire holders fixing a bone.

Referring to FIGS. 30 and 31, two other exemplary configurations are depicted. In FIG. 30, a bone 12 is fixed or secured at opposing ends relative to a single elongated member 16 using two pairs of extension finger assemblies 18 and screw pins 24, with the extension finger assemblies 18 extending perpendicular from the elongated member 16 on opposing sides and at generally diverging obtuse angles relative to one another to present fixation sites from which the screw pins 24 may extend into the bone 12 in a generally converging manner.

In FIG. 31, the opposing ends (or an end and an intermediate section) of a bone 12 are fixed or secured relative to a pair of rings 14 which are spaced apart and maintained in generally parallel planar orientation mounted on a pair of LCD bars 28, the bone 12 being fixed using an appropriate combination of either wire 26 or screw pins 24. It may be readily appreciated that the LCD bars 28 in FIG. 31 are in the lengthening-compression-distraction mode since no section of the bone 12 is fixed or secured to the central segment 132 as would occur in the transport mode.

The various components of the external fixation system 10 as described herein may be fabricated from any suitable material known to the art for use in such applications, including metallic or polymeric materials suitable for use in biomedical applications and compatible with tissue to which the components will be exposed or contact, and selected as dictated by known or experimentally-determined parameters relating to the suitable dimensions and mechanical stresses to which the components will be exposed during normal use as intended. The components may be finished or coated in any suitable manner using techniques known to the art to provide a workable and aesthetically pleasing surface, as well as to mitigate against certain deficiencies such as those caused by the exposure of certain metals or polymers to tissue or adverse environmental conditions. It may be appreciated that while a wide variety of known materials and finishes may be used, other materials or manufacturing processes hereafter developed or discovered may also be utilized to achieve the particular benefits and advantages associated with those materials, finishes, or processes.

In operation, the external fixation system 10 is fabricated and assembled as described above, and provided to a physician or other operator for the purpose of fixedly securing or therapeutically manipulating one or more bones 12 of a patient, either during setting and healing of fractures or breaks in those bones 12, subsequent to reconstructive surgery, to provide for realignment or programmed growth of the bones 12, or for any other procedure to which the external fixation system 10 may lend itself. The relevant components of the external fixation system 10 may be sterilized subsequent to manufacture and packaging, or prior to their use.

The various components of the external fixation system 10 may be assembled for a particular procedure in virtually any order or sequence which the operator finds convenient and practical to achieve the intended result, however it may be appreciated that for certain routine procedures it may be suitable for the operator to have some components mounted together in a predetermined configuration to expedite their use, or to assist in visualizing placement of pins or screws 24 or wire 26 relative to the bone 12 being acted upon.

Two steps in the method of using the external fixation system 10 which warrant particular note are the selection of the desired position for the elongated members 16 or wire holders 22 along the ring member 14, and the one-handed engagement of the extension finger members 18 relative to an elongated member 16 or the LCD bar 28.

Due to the intersecting apertures 106 defining the convoluted inner walls of the openings 104, the elongated members 16 or wire holders 22 may be spaced at closer adjacent intervals than if the apertures 106 did not intersect (thus forming a greater plurality of discrete openings 104), and greater control may be exercised over the radial positioning of the elongated members 16 or wire holders 22 which are spaced apart at non-adjacent locations or placeholders along the arc of the ring member 14.

Also as described above, once the extension finger member 18 is mounted on the elongated member 16 or LCD bar 28, the position and orientation of the screw 24 relative to the pin holder member 52—and the position and orientation of the pin holder member 52 relative to the body member 30 of the extension finger member 18—may be simultaneously clamped or secured in a desired configuration with a one-hand motion by tightening the securing member 60 carried on the pin holder member 52, thus allowing the operator's other hand to hold, manipulate, or orient other components of the external fixation system 10, the bone 12, or other tools or articles being utilized in the procedure.

While the preferred embodiments of the above external orthopedic fixation system 10 have been described in detail with reference to the attached drawings Figures, it is understood that the various depictions of alternate embodiments and configurations are shown for exemplary purposes only and do not limit the available applications or configurations in which the components of the external fixation system 10 may be utilized, and further that various changes, modifications, and adaptations may be made in the external orthopedic fixation system 10 without departing from the spirit and scope of the appended claims.

What is claimed is:

1. In an external fixation system for aligning an elongated member in a longitudinal direction generally parallel with a bone, said elongated member being mounted and secured in a desired position on a ring member, the improvement comprising:

the elongated member having a central segment with a pair of opposing ends, a pair of adjustment members each disposed on a corresponding one of said opposing ends, and a pair of sleeve members each disposed on a corresponding one of said pair of opposing ends, each of said pair of sleeve members being mounted moveably longitudinally relative to said central segment while constrained against rotation relative to said central segment and one another, each of said pair of sleeve members being adapted for operable connection to separate portions of the bone, such that rotation of at least one adjustment member in a first direction will cause the pair of sleeve members to move longitudinally relative to one another to exert a traction force upon the bone, and such that rotation of the at least one adjustment member in a second direction opposing said first direction will cause the pair of sleeve members to move longitudinally relative to one another to exert a compressive force upon the bone.

2. The improvement of claim 1 wherein each of the pair of sleeve members is slidably mounted on the corresponding end of the central segment, the central segment defines a pair of threaded regions, and said adjustment members comprise a pair of threaded end members each engagingly mounted on one of said pair of threaded regions and disposed at corresponding ones of the pair of opposing ends, each of the pair of sleeve members being operatively connected to a corresponding one of said pair of threaded end members, such that rotation of said pair of threaded regions relative to said pair of threaded end members will move the pair of sleeve members longitudinally relative to the central segment, thereby accomplishing a lengthening-compression-distraction mode for the external fixation system.

3. The improvement of claim 2 wherein each of the threaded end members may be actuated to displace the pair of sleeve members axially outward a small distance relative to the central segment such that the pair of sleeve members may shift freely relative to the central segment through said small distance, whereby dynamization of the external fixation system may be accomplished by placing weight-bearing pressure on the bone which is absorbed by the bone through shifting of the pair of sleeve members relative to one another or to the central segment.

4. The improvement of claim 1 wherein each of the pair of sleeve members is slidably mounted on the corresponding end of the central segment and the sleeve members are separated by a spacing distance, each of the pair of sleeve members being operatively connected to one of the adjustment members such that rotation of at least one of said adjustment members or the central segment moves the central segment longitudinally relative to the pair of sleeve members without substantially altering said spacing distance between the pair of sleeve members, thereby accomplishing a transport mode for the external fixation system.

5. In an external fixation system for aligning a bone, the improvement comprising:

an elongated member having a central segment with two opposing end portions;

at least one adjustment member disposed on at least one of the opposing end portions; and at least two sleeve members each disposed on a corresponding one of the two opposing end portions, the at least two sleeve members further being mounted moveably longitudinally relative to the central segment and being adapted for operative connection to a portion of the bone wherein rotation of the at least one adjustment member causes at least one of the at least two sleeve members to move longitudinally relative to said central segment and exert a force upon the bone.

6. The improvement of claim 5 further including:

a pin and a longitudinal slot associated with each of the at least two sleeve members and the central segment, each pin extending radially from one of the central segment and its associated sleeve member into its associated longitudinal slot, said longitudinal slot being formed in the other of the central segment and associated sleeve member.

7. The improvement of claim 5 wherein the at least two sleeve members are constrained against rotation relative to the central segment.

8. The improvement of claim 5 wherein rotation of the at least one adjustment member causes the at least two sleeve members to move longitudinally to exert said force upon the bone.

* * * * *